US011944364B2

(12) United States Patent
Andersen

(10) Patent No.: US 11,944,364 B2
(45) Date of Patent: Apr. 2, 2024

(54) CABLE-LOCKING PLATE WITH SCREW

(71) Applicant: Orthopedic Designs North America, Inc., Tampa, FL (US)

(72) Inventor: Romney C Andersen, Newport News, VA (US)

( * ) Notice: Subject to any disclaimer, the term of this patent is extended or adjusted under 35 U.S.C. 154(b) by 466 days.

(21) Appl. No.: 17/218,600

(22) Filed: Mar. 31, 2021

(65) Prior Publication Data
US 2021/0307802 A1   Oct. 7, 2021

Related U.S. Application Data

(60) Provisional application No. 63/100,816, filed on Apr. 3, 2020.

(51) Int. Cl.
A61B 17/80 (2006.01)
A61B 17/68 (2006.01)
(Continued)

(52) U.S. Cl.
CPC .......... A61B 17/8869 (2013.01); A61B 17/80 (2013.01); A61B 17/842 (2013.01); A61B 17/0401 (2013.01); A61B 2017/0451 (2013.01); A61B 2017/0618 (2013.01); A61B 2017/681 (2013.01); A61B 17/7022 (2013.01); A61B 17/7053 (2013.01); A61B 17/8057 (2013.01);
(Continued)

(58) Field of Classification Search
CPC ....... A61B 17/80; A61B 17/82; A61B 17/842; A61B 17/8085; A61B 17/8061; A61B 17/8861; A61B 17/823; A61B 17/8869; A61B 17/8057; A61B 17/826; A61B 17/7053; A61B 17/0401; A61B 17/06166; A61B 17/1796; A61B 17/7022; A61B 2017/681; A61B 2017/00663; A61B 2017/0618; A61B 2017/0414; A61B 2017/0451; A61B 2017/0454; A61B 2017/0456; F16G 11/00; F16G 11/101; F16G 11/14
USPC ........ 606/86 R, 280, 282, 285, 74, 105, 103
See application file for complete search history.

(56) References Cited

U.S. PATENT DOCUMENTS

| 5,415,658 A * | 5/1995 | Kilpela | ................ A61B 17/842 606/300 |
| 6,086,608 A * | 7/2000 | Ek | ..................... A61B 17/0487 606/301 |

(Continued)

*Primary Examiner* — Marcela I. Shirsat
(74) *Attorney, Agent, or Firm* — Larson & Larson; Justin P. Miller; Frank Liebenow

(57) ABSTRACT

The cable-locking plate with screw allows for compression of bone fractures using a tensioned cable. The cable-locking plate with screw allows the use of a cable as a flexible bridging member, such as a cable, helps create compression while accommodating the unusual shape. The cable-locking plate with screw allows a surgeon to tension a cable through the plate, then grip the cable by tightening a screw associated with the plate. The compression is created is across the fracture, not around the bone, thus avoiding compression of nerve and blood vessels along the bone's surface. The cable is guided into an ideal position using cable channels, allowing the surgeon to concentrate on tension and screw compression. The plate and cable system are then left in the patient while the bone mends. The cable-locking plate with screw is either left permanently or removed during a later surgery.

18 Claims, 5 Drawing Sheets

(51) Int. Cl.
*A61B 17/82* (2006.01)
*A61B 17/84* (2006.01)
*A61B 17/86* (2006.01)
*A61B 17/88* (2006.01)
A61B 17/04 (2006.01)
A61B 17/06 (2006.01)
A61B 17/70 (2006.01)

(52) U.S. Cl.
CPC .......... *A61B 17/8061* (2013.01); *A61B 17/82* (2013.01); *A61B 17/863* (2013.01); *A61B 17/8861* (2013.01)

(56) References Cited

U.S. PATENT DOCUMENTS

| | | | | |
|---|---|---|---|---|
| 2002/0188297 | A1* | 12/2002 | Dakin | A61B 17/842 606/103 |
| 2011/0144699 | A1* | 6/2011 | Fallin | A61F 2/30739 623/18.11 |
| 2014/0194907 | A1* | 7/2014 | Bonutti | A61B 17/0401 606/151 |
| 2015/0045836 | A1* | 2/2015 | Leuenberger | A61B 17/8047 606/281 |
| 2016/0038199 | A1* | 2/2016 | Wiederkehr | A61B 17/8861 606/74 |
| 2019/0350629 | A1* | 11/2019 | Larsen | A61B 17/0401 |

* cited by examiner

CABLE-LOCKING PLATE WITH SCREW

CROSS-REFERENCE TO RELATED APPLICATION

This application is a continuation-in-part of U.S. Pat. App. Ser. No. 63/100,816, filed Apr. 3, 2020.

FIELD

This invention relates to the field of bone fracture devices and more particularly to a device for closing a bone fracture using a tensioned cable.

BACKGROUND

Treatment of a bone fracture often involves immobilization. The manner of immobilization varies depending on the shape and type of fractured bone. Long bones can be cast, and small bones either cast or wrapped.

Alternatively, or additionally, certain fractures are best treated with implanted hardware, such as plates or screws.

But certain types of bone fractures are difficult to immobilize using these traditional techniques. For example, fractures of the patella/kneecap.

What is needed is a device for compression of fractures of bones that are difficult to immobilize using traditional hardware.

SUMMARY

The cable-locking plate with screw allows for compression of bone fractures using a tensioned cable.

The prior art uses screws affixed directly to the bone. This is difficult for non-linear bones, or when the holes could overly compromise the structural integrity of the bone.

As a result, certain fractures are difficult to close and compress using screws. Specially, the patella, or kneecap, is difficult to surround with a cast, and a difficult shape to bridge with a screw or fastener.

The cable-locking plate with screw allows the use of a cable, suture, or other flexible bridging member, to create compression while accommodating the unusual shape.

But the use of a cable creates the secondary issue of maintaining tension after the surgery.

The cable-locking plate with screw allows a surgeon to tension a cable through the plate, then grip the cable by tightening a screw associated with the plate. The compression is created is across the fracture, not around the bone, thus avoiding compression of nerve and blood vessels along the surface of the bone.

The cable is guided into an ideal position using cable channels, allowing the surgeon to concentrate on tension and screw compression.

The plate and cable system are then left in the patient while the bone mends. The cable-locking plate with screw is either left permanently or removed during a later surgery.

The process of placement of the cable-locking plate with screw is as follows:

The fracture at issue is exposed;
Placement of the cable-locking plate with screw is determined;
Holes are drilled through the bone for passage of the cables;
The fracture is compressed;
The first plate is placed;
The cable or cables are passed through the first plate, and through the holes;
The cable or cables are locked with respect to the first plate;
The second plate is placed;
The cable or cables tensioned; and
The cable or cables are locked with respect to the second plate.

The plates are optionally bent around the bone, thus allowing the first and second plate to be the same plate, the cable passing in and out of the plate at different locations.

BRIEF DESCRIPTION OF THE DRAWINGS

The invention can be best understood by those having ordinary skill in the art by reference to the following detailed description when considered in conjunction with the accompanying drawings in which.

DETAILED DESCRIPTION

Figure 1:
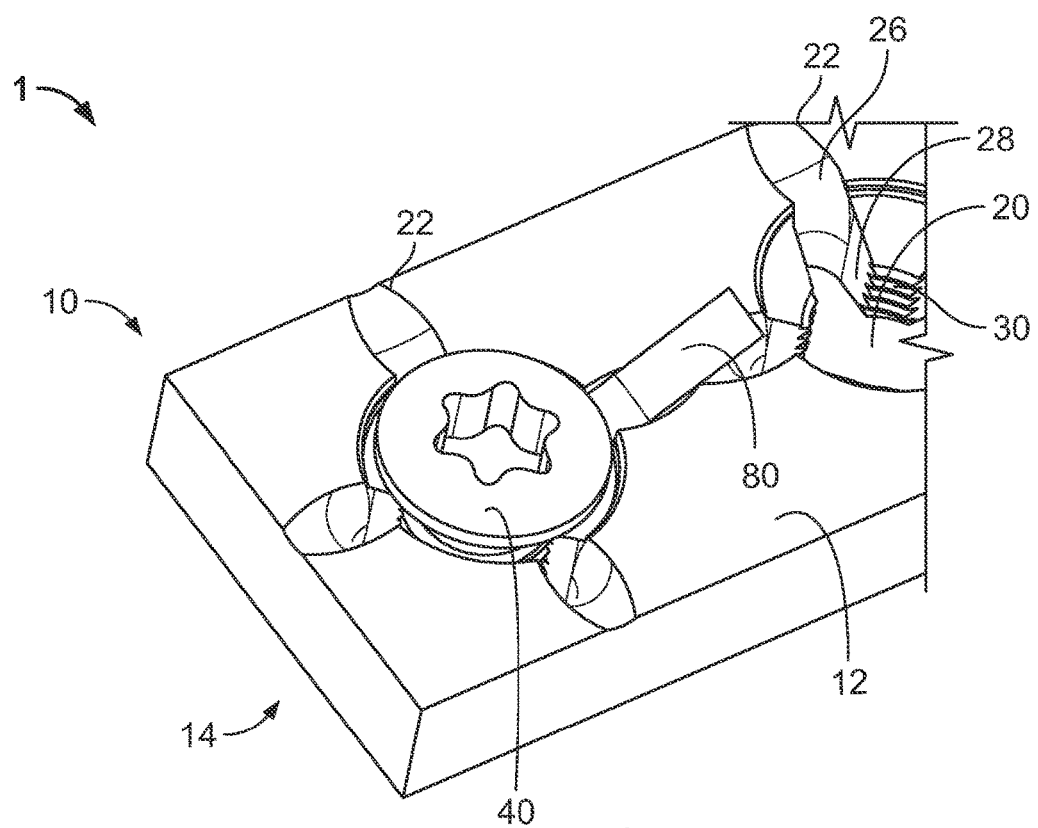
FIG. 1 illustrates a first isometric view of the cable-locking plate with screw.

Reference will now be made in detail to the presently preferred embodiments of the invention, examples of which are illustrated in the accompanying drawings. Throughout the following detailed description, the same reference numerals refer to the same elements in all figures.

Figure 2:
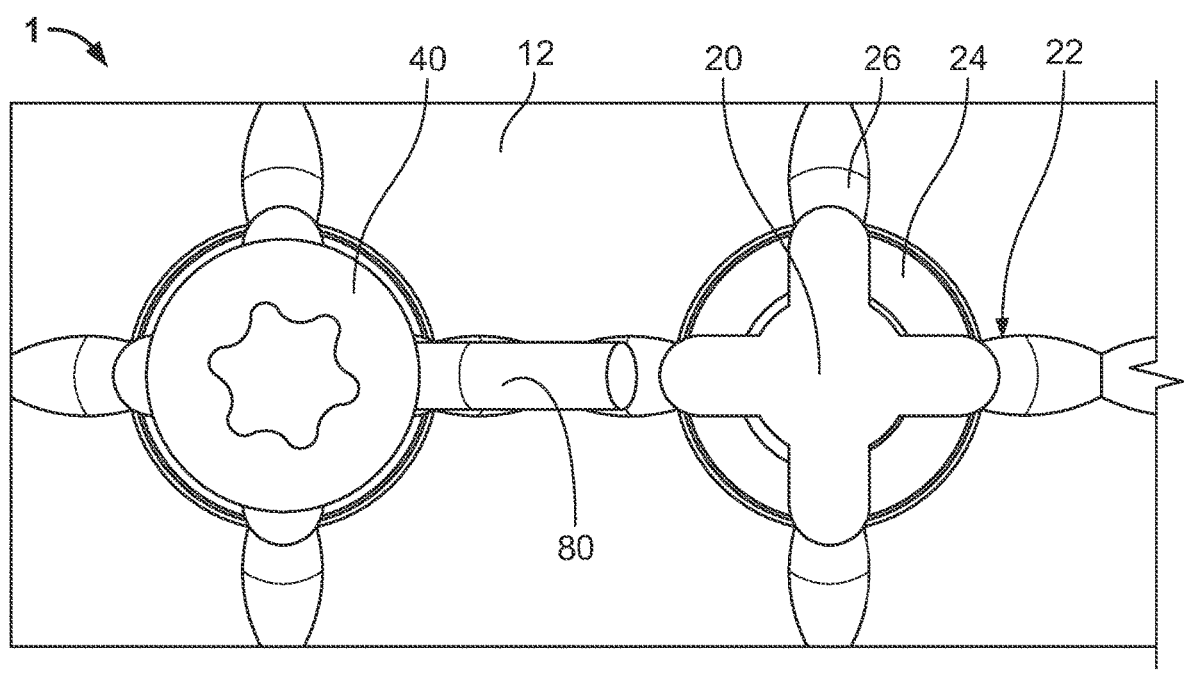
FIG. 2 illustrates a top view of the cable-locking plate with screw.

Referring to FIGS. 1 and 2, a first isometric view and a first top view of the cable-locking plate with screw are shown.

The cable-locking plate with screw 1 includes a plate 10 with an upper surface 12 and a lower surface 14.

One or more holes 20 pass through the plate 10.

Each hole 20 includes a recessed groove 24 that rings the hole 20, the recessed groove 24 interrupted by the cable channels 22. Each cable channel 22 optionally includes a sloping interface 26 that interfaces with the cable 80. The cable 80 is held in position between groove walls 28.

The hole 20 includes threads 30 that interface with screw 40.

The cable channels 22 are shown placed at 0 degrees, 90 degrees, 180 degrees, and 270 degrees, but other angular orientations are anticipated.

Figure 3:
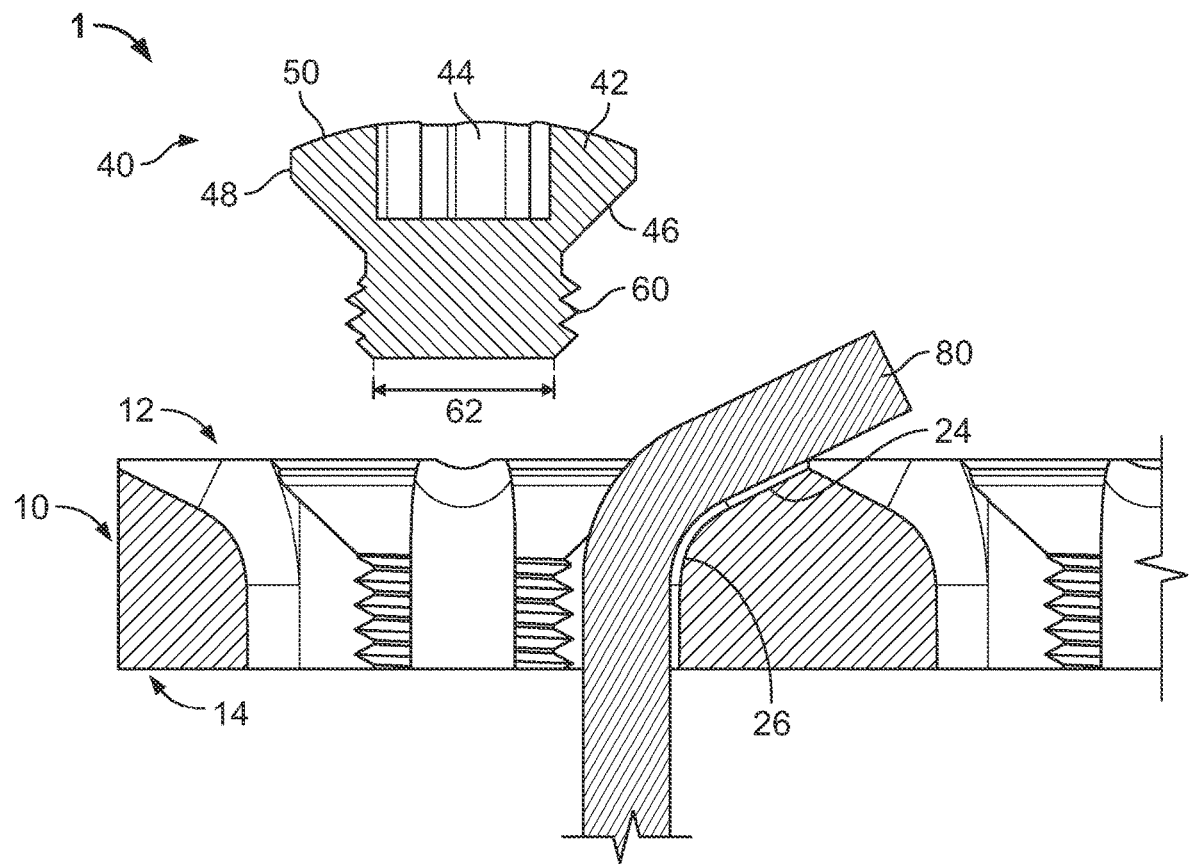
FIG. 3 illustrates a cross-sectional view, before screw placement, of the cable-locking plate with screw.
Figure 4:
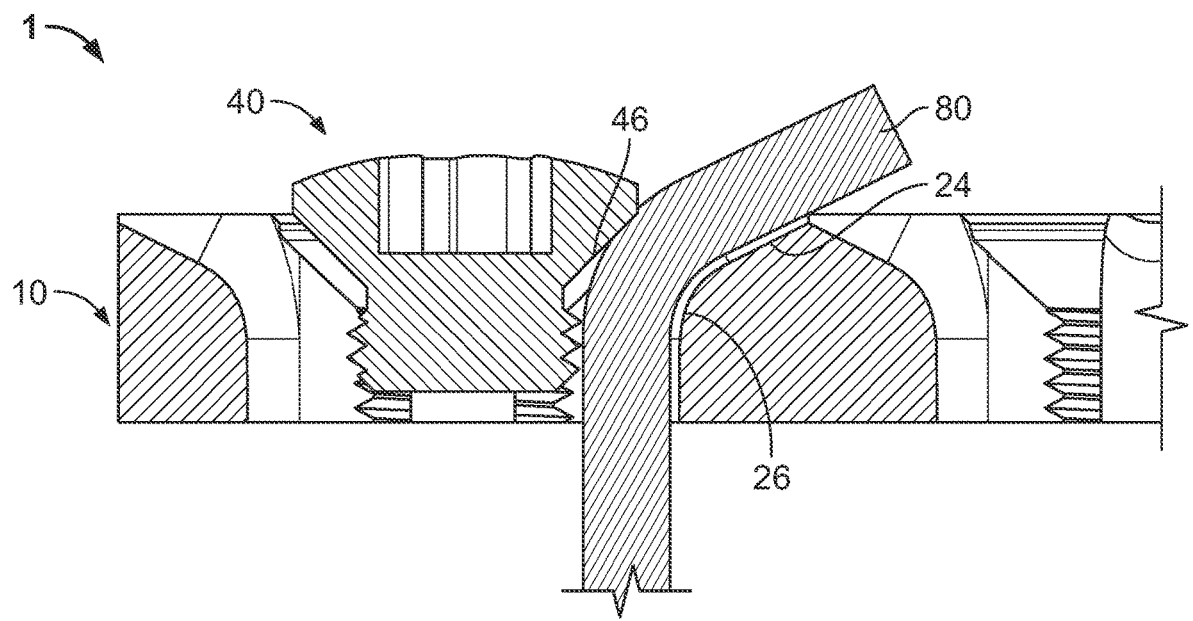
FIG. 4 illustrates a cross-sectional view, after screw placement, of the cable-locking plate with screw.

Referring to FIG. 3, a cross-sectional view, before screw placement, and FIG. 4, a cross-sectional view, after screw placement, of the cable-locking plate with screw are shown.

The cable-locking plate with screw 1 is shown before the screw 40 has locked the cable 80 to the plate 10.

The screw 40 includes a screw head 42, drive 44, lower head surface 46, circumferential head surface 48, and upper head surface 50.

The screw 40 further includes a first set of threads 60 with a first diameter 62.

The cable 80 rests against the sloping interface 26 of the recessed groove 24. The sloping interface 26 creates a descending angle for the cable 80 with respect to the upper surface 12 of the plate 10. The descending angle allows the suture to protrude beyond the screw head 42, while also passing through the lower surface 14 of the plate immediately adjacent to the first set of threads 60 of the screw 40.

As the screw 40 is tightened into the plate 10, the lower head surface 46 of the screw head 42 compresses the cable 80 against the sloping interface 26 of the recessed groove 24, holding the cable 80 in place.

Figure 5:
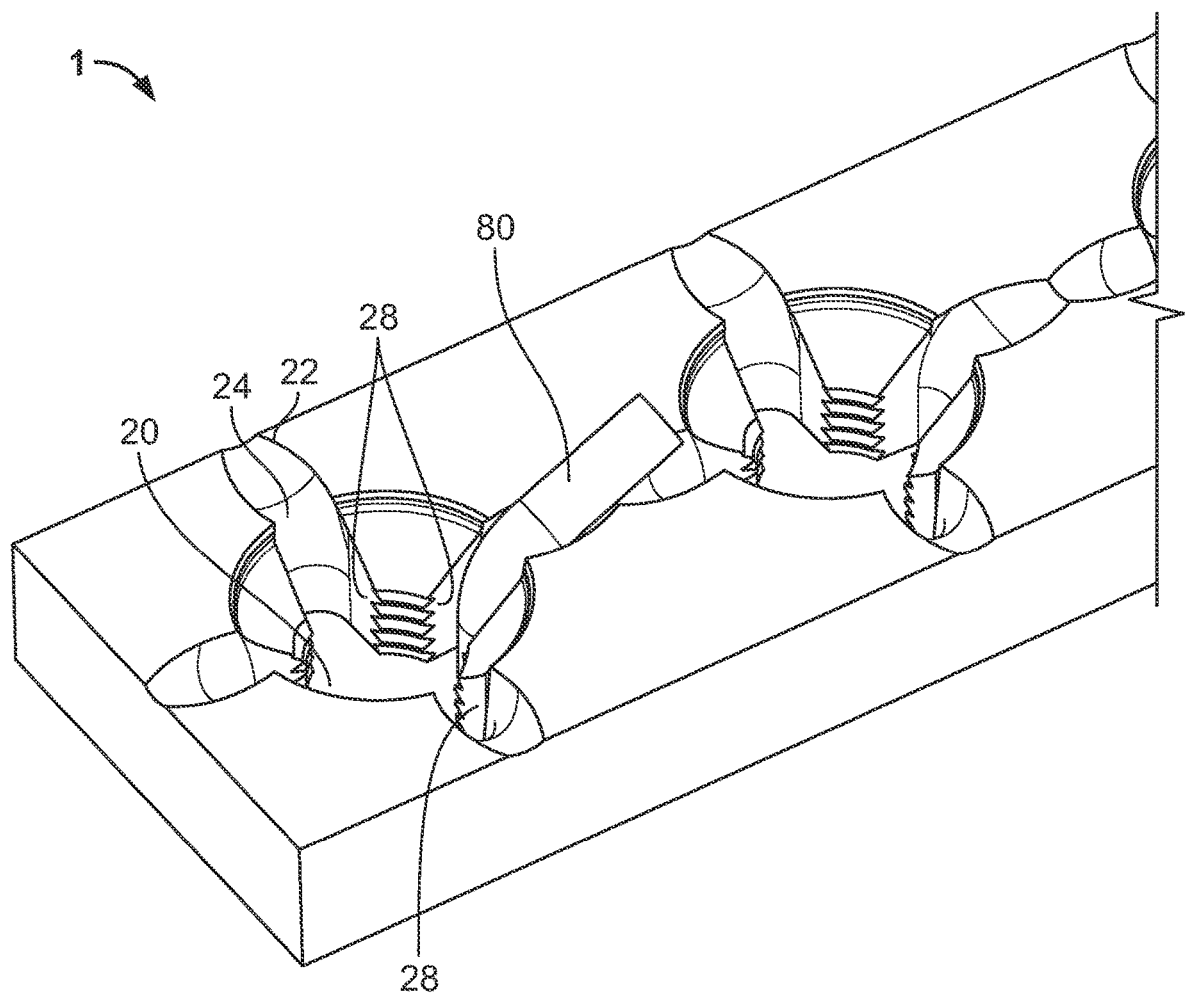
FIG. 5 illustrates a second isometric view, without the screw, of the cable-locking plate with screw.

Referring to FIG. 5, a second isometric view, without the screw, of the cable-locking plate with screw is shown.

The cable 80 is shown held in place within the cable channel 22, and resting within the recessed groove 24. The cable 80 then follows and bends around the sloping interface 26.

The groove walls 28 of the recessed groove 24 hold the cable 80 in place as the screw head 42 rotates against the cable 80. The cable 80 is thus maintained parallel to the hole 20, rather than being twisted by rotation of the screw 40.

Figure 6:
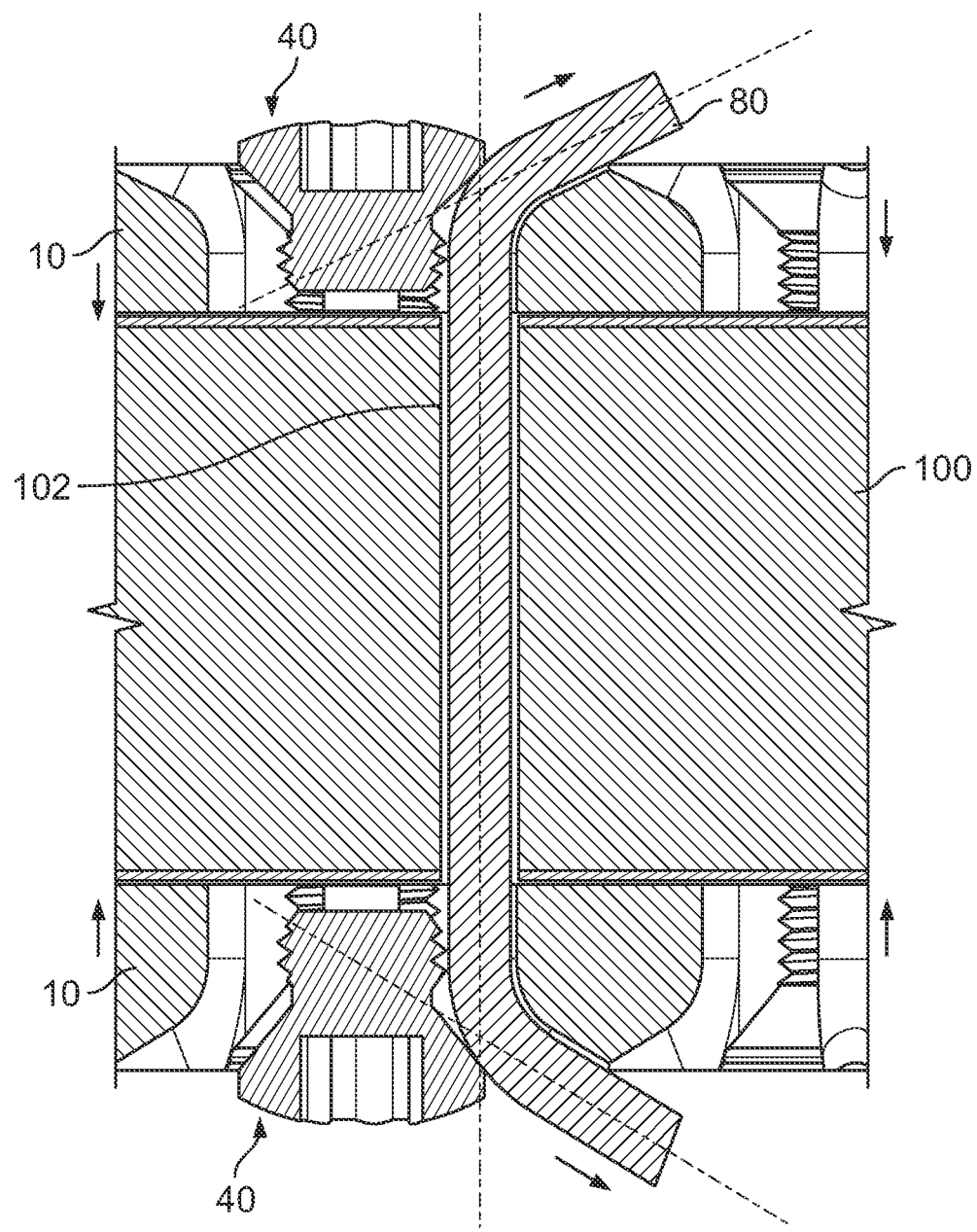
FIG. 6 illustrates a cross-sectional view, showing tensioning across a bone, of the cable-locking plate with screw.

Referring to FIG. 6, a cross-sectional view, showing tensioning across a bone, of the cable-locking plate with screw is shown.

The cable 80 passes through the bone hole 102 of the bone 100.

The cable is affixed at both ends, held by screws 40 against plates 10. The result is compression of the bone 100 by the plates 10, closing any fracture.

Figure 7:
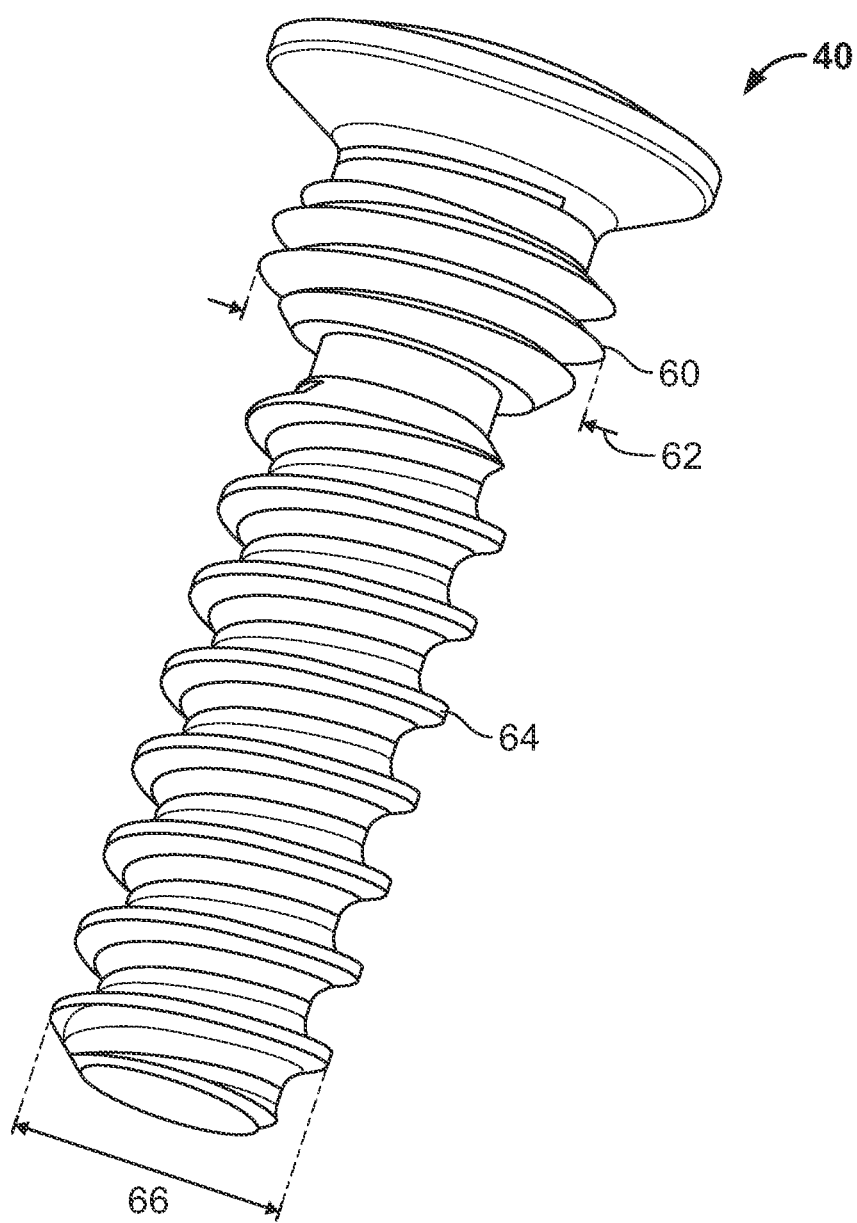
FIG. 7 illustrates a second embodiment of the screw of the cable-locking plate with screw.

Referring to FIG. 7, a second embodiment of the screw of the cable-locking plate with screw is shown.

In this embodiment, the screw 40 includes a first set of threads 60 with a first diameter 62, and a second set of threads 64 with a second diameter 66.

The first set of threads 60 interfaces with the plate 10 (see FIG. 6), and the second set of threads interfaces with the bone 100 (see FIG. 6). This allows the screw 40 to both compress the cable 80 (see FIG. 6) and directly connect to the bone 100.

Equivalent elements can be substituted for the ones set forth above such that they perform in substantially the same manner in substantially the same way for achieving substantially the same result.

It is believed that the system and method as described and many of its attendant advantages will be understood by the foregoing description. It is also believed that it will be apparent that various changes may be made in the form, construction, and arrangement of the components thereof without departing from the scope and spirit of the invention or without sacrificing all of its material advantages. The form herein before described being merely exemplary and explanatory embodiment thereof. It is the intention of the following claims to encompass and include such changes.

What is claimed is:

1. A device to create compression across a bone fracture using a cable placed under tension, the device comprising:
   one or more plates, the one or more plates including a first hole and a second hole;
      each plate of the one or more plates the plate including an upper surface and a lower surface;
      a first cable channel parallel to the first hole;
      a second cable channel parallel to the second hole;
      a cable passing through the first cable channel and the second cable channel;
      the cable passing through the first hole and the second hole;
   a first screw that threads into the first hole and a second screw that threads into the second hole;
      the first screw including a first head;
      the second screw including a second head;
      the first screw, within the first hole, compressing the cable against the first cable channel to maintain a position of the cable with respect to the first cable channel;
      the second screw, within the second hole, compressing the cable against second cable channel to maintain the position of the cable with respect to the second cable channel;
   whereby a user places the cable within the first cable channel and the second cable channel, optionally tensions the cable, and locks the cable in position using the first screw.

2. The device to create compression across a bone fracture using a cable placed under tension of claim 1, wherein:
   the first cable channel is set at a descending angle with respect to the upper surface of one or more plates;
      the first cable channel guiding a bend of the cable as the cable passes under the first head of the first screw;
   whereby the first cable channel holds the cable in a position where the cable does not interfere with the first screw as the first screw threads into the one or more plates.

3. The device to create compression across a bone fracture using a cable placed under tension of claim 2, wherein the first cable channel further comprises:
   two or more groove walls;
      the two or more groove walls supporting sides of the cable, preventing the cable from rotating as the first head of the first screw descends, the first head of the first screw rubbing the cable as the first screw creates compression against the cable;
   whereby the two or more groove walls prevent rotational motion of the cable with respect to the first hole.

4. The device to create compression across a bone fracture using a cable placed under tension of claim 1, wherein the first cable channel further comprises:
   two or more groove walls;
      the two or more groove walls supporting sides of the cable, preventing the cable from rotating as the first head of the first screw descends, the first head of the first screw rubbing the cable as the first screw creates compression against the cable;
   whereby the two or more groove walls prevent rotational motion of the cable with respect to the first hole.

5. The device to create compression across a bone fracture using a cable placed under tension of claim 1, wherein:
   the first cable channel is four cable channels, set at angles of 0, 90, 180, and 270 with respect to the first hole;
   whereby having four cable channels allows the user to select an idea position for the cable as it passes through the one or more plates.

6. The device to create compression across a bone fracture using a cable placed under tension of claim 1, wherein the first head of the first screw further comprises:
   a lower head surface;
      the lower head surface in contact with the cable during compression of the cable.

7. A device for compression of a fracture in a bone, the device comprising:
   a first plate for placement against the bone;
      the first plate including a first hole;
   a second plate for placement against the bone;
      the second plate including a second hole;

a first screw;
   the first screw including a first head;
   the first screw threading into the first hole;
a second screw;
   the second screw including a second head;
   the second screw threading into the second hole;
a first cable channel adjacent the first hole;
a second cable channel adjacent the first hole;
a cable passing through the first cable channel parallel to the first hole, and the cable passing through the second cable channel parallel to the second hole;
   the first cable channel and the second cable channel to guiding the cable to a position adjacent to the first head and the second head;
whereby threading the first screw into the first hole reduces a distance between the first head and the first cable channel.

8. The device for compression of a fracture in a bone of claim 7, wherein:
the first cable channel is set at a descending angle with respect to upper surface;
   the first cable channel guiding a bend of the cable as the cable passes under the first head of the first screw;
whereby the first cable channel holds the cable in a position where the cable does not interfere with the first screw as the first screw threads into the first plate.

9. The device for compression of a fracture in a bone of claim 8, wherein the first cable channel further comprises:
two or more groove walls;
   the two or more groove walls supporting sides of the cable, preventing the cable from rotating as the first head of the first screw descends, the first head of the first screw rubbing the cable as the first screw creates compression against the cable;
whereby the two or more groove walls prevent rotational motion of the cable with respect to the first hole.

10. The device for compression of a fracture in a bone of claim 7, wherein the first cable channel further comprises:
two or more groove walls;
   the two or more groove walls supporting sides of the cable, preventing the cable from rotating as the first head of the first screw descends, the first head of the first screw rubbing the cable as the first screw creates compression against the cable;
whereby the two or more groove walls prevent rotational motion of the cable with respect to the first hole.

11. The device for compression of a fracture in a bone of claim 7, wherein:
the first cable channel is four cable channels, set at angles of 0, 90, 180, and 270 with respect to the first hole;
whereby having four cable channels allows a user to select an idea position for the cable as it passes through the first plate.

12. The device for compression of a fracture in a bone of claim 7, wherein the first head of the first screw further comprises:
a lower head surface;
   the lower head surface in contact with the cable during compression of the cable.

13. A device for compressing a bone fracture comprising:
a first plate with a first cable groove;
   the first cable groove adjacent to a first threaded hole in the first plate;
   the first cable groove parallel to the first threaded hole;
a second plate with a second cable groove;
   the second cable groove adjacent to a second threaded hole in the first plate;
   the second cable groove parallel to the second threaded hole;
a first screw;
   the first screw interfacing with the first threaded hole via threads;
   the first screw including a first head;
   rotation of the first screw into the first plate causing the first head to compress a cable in the first cable groove;
whereby a user creates tension in the cable, then causes the first screw to compress the cable against the first plate, thus maintaining the tension.

14. The device for compressing a bone fracture of claim 13 wherein:
the first cable groove is set at a descending angle with respect to a first upper surface of the first plate;
   the first cable groove guiding a bend of the cable as the cable passes under the first head of the first screw;
whereby the first cable groove holds the cable in a position where the cable does not interfere with the first screw as the first screw threads into the first plate.

15. The device for compressing a bone fracture of claim 14, wherein the first cable groove further comprises:
two or more groove walls;
   the two or more groove walls supporting sides of the cable, preventing the cable from rotating as the first head of the first screw descends, the first head of the first screw rubbing the cable as the first screw creates compression against the cable;
whereby the two or more groove walls prevent rotational motion of the cable with respect to the first threaded hole.

16. The device for compressing a bone fracture of claim 13, wherein the first cable groove further comprises:
two or more groove walls;
   the two or more groove walls supporting sides of the cable, preventing the cable from rotating as the first head of the first screw descends, the first head of the first screw rubbing the cable as the first screw creates compression against the cable;
whereby the two or more groove walls prevent rotational motion of the cable with respect to the first threaded hole.

17. The device for compressing a bone fracture of claim 13, wherein:
the first cable groove is four cable channels, set at angles of 0, 90, 180, and 270 with respect to the first threaded hole;
whereby having four cable grooves allows the user to select an idea position for the cable as it passes through the first plate.

18. The device for compressing a bone fracture of claim 13, wherein the first head of the first screw further comprises:
a lower head surface;
   the lower head surface in contact with the cable during compression of the cable.

* * * * *